United States Patent [19]

Turmes, Jr.

[11] Patent Number: Plant 5,847

[45] Date of Patent: Jan. 6, 1987

[54] VARIEGATED LEMON-LIME TREE NAMED LEMONINE

[76] Inventor: Nicolas A. Turmes, Jr., 144 NW. 20 St., Homestead, Fla. 33030

[21] Appl. No.: 635,499

[22] Filed: Jul. 30, 1984

[51] Int. Cl.[4] ..... A01H 5/03

[52] U.S. Cl. ..... Plt./45

[58] Field of Search ..... Plt./45

[56] References Cited

PUBLICATIONS

Advances in Fruit Breeding, Janick et al, 1975, Purdue Univ. Press, W. Lafayette, Ind., p. 531 cited.

*Primary Examiner*—R. E. Bagwill

*Attorney, Agent, or Firm*—John Cyril Malloy

[57] ABSTRACT

A citrus tree producing lemon-lime combination fruits and ample foliage wherein both foliage and fruits are variegated, such variegation of both arising from the type of bud variation known as white-over-green periclinal chimera.

3 Drawing Figures

BACKGROUND OF THE INVENTION

This invention relates to a new and distinctive variety of citrus tree and its fruits including a variegated lemon-lime hybrid, discovered by me in a cultivated grove on my property located in the City of Homestead, in the County of Dade, and the State of Florida. This lemon-lime variety may be referred to as its cultivar name Variegated Lemonine (Variegated Lemon×Lime) which was discovered as a chance, natural limb mutation that originated from a lemon-lime tree which is the subject of U.S. Plant Pat. No. 3,292, on my property as set forth above, but distinguishable therefrom by having fruit and foliage which are chimeral or variegated in appearance.

Careful botanical and horticultural study of this new tree and its fruits confirms that it exhibits the kind of variegation that arises from the type of bud-variation known as a white-over-green periclinal chimera, and that it represents a new variety of lemon-lime hybrid. My new variegated lemon-lime tree is propagated vegetatively and I have propagated it by air layering, and budding on commonly employed root stocks therefor. The subject lemon-lime tree provides a novel ornamental pot plant or door yard tree and further provides a novel juice producing acid citrus fruit, the juice of which can be used fresh, frozen or processed in any manner comparable to the various ways in which lemon or lime juice are processed and further wherein the variegation of both the foliage and the fruits provides novel and aesthetically pleasing plants.

FIG. 1 shows a plant of the new variety;

FIG. 2 shows a fruit; and

FIG. 3 shows fruit and foliage.

TECHNICAL DESCRIPTION

The Tree

The tree is small, spreading, evergreen, productive, rather compact and similar in habit and general appearance to trees of unvariegated lemon-lime hybrids, but less vigorous amd more slow-growing.

The leaves are alternate, unifoliate, with a distinct articulation between the petiole and the leaf blade. Petioles are short, normally 10 mm or less in length, commonly less than 3 mm wide and margined whereat the margins are 1 mm or less wide. Leaf blades are commonly oval to elliptically oval and rarely obovate or oblanceolate. The base of the blade is obtuse to cuneate and often somewhat oblique. The blade tips are usually acute to acuminate, but occasionally obtuse, cuspidate, or aristate and rarely retuse or emarginate. In most leaves, the two portions of the blade lying right and left of the midrib are developed or expanded asymmetrically so that the blade is somewhat distorted but rarely strongly distorted and sickle-shaped. Blades are commonly from 70 to 98 mm long and from 37 to 53 mm wide at the broadest portion of the blade. Leaves produced at the beginning of a growth cycle are often much smaller being from 15 to 25 mm overall length and their blades are usually strongly asymmetrical. Leaf blades on suckers or watersprouts are larger, up to 132 mm or more long, and 78 mm or more broad. Margins of the blade are finely serrulate and the errations are irregular and shallow. Oil glands in the blade are numerous, inconspicuous, tine and only apparent as minute pelucid dots when the blade is held up to the light. The leaf midrib is conspicuous above but not prominent below and the leaf blades are glaucous and thin.

The leaves have a highly irregular and incomplete white marginal zone, the white areas often being much dwarfed. (Although customarily referred to as white, these non-green tissues and areas may vary in color from creamy white to light yellow). The upper side of the blade often shows as many as three different tints or shades of green and the patterns of variegation of green shades is mainly independent between the upper and lower sides of the blade. These lighter green regions are extremely irregular and variable. Occasionally a shoot is completely white, nearly or quite throughout one growth cycle. No completely green unvariegated shoots are produced, but occasionally a shoot produces leaves mostly of a single shade of green, with very narrow irregular white margins. These latter shoots may give rise to highly variegated shoots in subsequent growth cycles.

Thorns are few or absent on new growth originating on the older mature portions of the crown of the tree. Solitary, sharp-pointed, slender, axillary thorns are present on juvenile growth, averaging 5 mm in length and 1 mm or less in width at their base. Axillary thorns on watersprouts or suckers are much larger and are stout, sharp-pointed, terete and up to 35 mm or more in length. Their bases are flattened being about 5 mm wide and 2.5 to 3 mm thick.

Flowers mostly perfect (bisexual), occasionally male from abortion of the pistil and either solitary in the leaf axils or borne in few-flowered cymose axillary or terminal racemes. Flower buds are medium sized averaging 20 mm in overall length in aestivation and pinkish-purple in color. The pedicel is short being about 10 mm long. Sepals, 4 or 5, are fused forming a small cup-like calyx 3 to 4 mm deep and 5 to 7 mm in diameter. Both the pedicel and calyx are light green in color and partially or wholly flushed with reddish-purple. The tips of the calyx lobes are blunt but strongly mucronate. There are petals, 4 or 5, being strap-shaped and having the tips obtuse, acute, or acuminate and not clawed at the base and imbricate in the bud, averaging 20 mm long and 7 mm wide. The adaxial (upper) surface is white and the abaxial surface is reddish-purple. There are 5 or 6 times as many stamens as petals which are polyadelphous, with the filaments cohering along a part or along most of their length into a few bundles. The stamens are inserted beneath the disk. The filaments are white, and anthers bright yellow with pollen being abundant and bright yellow. The disk is small, green and cup-shaped, enclosing the base of the ovary. The pistil is small having an average length of 13 mm; ovary globose, 3 to 4 mm high and being somewhat tapered at the top but clearly delineated from the deciduous style and cream or light green in color. The style is cylindrical having an average length of 7 mm and being cream-colored. Stigma capitate is nearly as large as the ovary and is bright yellow (the same color as the anthers). The fragrance is sweet, pleasing and suggestive of orange blossoms.

The Fruit

External Fruit Characters

The immature fruits have abundant, rather indefinite narrow longitudinal stripes of thin whitish and normal green rind and occasionally there is a wider and well-defined sector of whitish rind. The fruit reaches maturity, that is full size, juiciness and with fully formed and mature seeds while still retaining this green and white striped coloration. If the fruit is permitted to remain on the tree after becoming full-sized, this coloration continues. The surface of the fruit is medium smooth, with slight depressions over the largest oil glands and the surface is very faintly ribbed and glossy. The shape of the fruit is round to obovate or oval and symmetrical. The size is medium and 45 to 55 mm in diameter having an overall height of 50 to 70 mm. The base is evenly rounded and sometimes very slightly ribbed and furrowed and rarely very slightly necked. Calyx persistent, even, small irregularly divided divisions short and lobes are blunt, thin, with persistent tips, mucronate. A small stem is apparent being 3 mm or less in diameter. The apex is evenly rounded, very faintly nippled and the nipple is less than 10 mm in diameter and about 5 mm high. Aerole is inconspicuous and is even indistinct. Style is deciduous; stylar scar small being 2 mm or less in diameter and is either even or faintly protruded. If protruded, such is less than 0.5 mm.

Internal Fruit Characteristics

The rind is then being 3.5 to 5 mm and averaging 4 mm in median cross-section and further being firm, adherence to medium-strong, and no puffiness. Oil glands are numerous, small, inconspicuous and about 64 in number per square centimeter of surface and primary glands extending vertical to surface are globose to abovoid, small, average diameter parallel to the surface 1 mm, with surface slightly depressed and contour between primary glands even. Oil is not abundant but highly volatile when released, aroma strong and rank when the oil is first released having lime and orange tones. The aroma quickly fades to a mild grapefruit-like odor on evaporation. The glandular layer is then comprising from 25 to 33 percent of the thickness of the rind and is variegated being green and white striped longitudinally. The variegation is restricted to the glandular layer. Mesocarp (albedo) is thin, white, vascular bundles are inconspicuous and texture is medium-soft. Axis in median cross-section is round to oval, small, solid, white, average mid-diameter 6 mm. There are from 10 to 12 segments, usually 10 or 11 having medium to strong adherence and little rag from rind. The septa is then, relatively tough, and having dorsal contour convex. The pulp is uniformly white, curing to a pale golden yellow in color, fine-grained and tender in texture. The vesicles are small and slender and juicy. Juice is strongly acidic, bitterness slight or none and the aroma weak and indefinite. Flavor is mostly sour with faint indefinite overtones and no after-taste. Perfect seeds are medium-sized, plump, average length 10.8 mm, average width 7.5 mm and ovate, slightly angular at the placental end. The surface is smooth, strongly veined and the outer seed coat is cream-colored and translucent. The inner seed coat varies in color from light brown to reddish or purple. Chalazal spot is dark purplish and cotyledons is light green. Imperfect seeds are mostly very small being less than 5 mm long and brownish. Imperfect seeds are occasionally as long as perfect seeds and similarly colored, but flattened. The degree of seediness varies from fruit to fruit and from one crop to another. Some sets of fruit are mostly seedy with from 12 to 20 perfect seeds per fruit. Other sets are largely seedless.

Of other known lemon-lime combinations of which I am aware, my tree is the only one that produces variegated foliage and fruits.

What is claimed is:

1. A new and distinct variety of lemon-lime hybrid citrus tree, substantially as herein shown and described characterized particularly as to novelty by foliage and fruits both being variegated, said variegation arising from the type of bud variation known as white-over-green periclinal chimera.

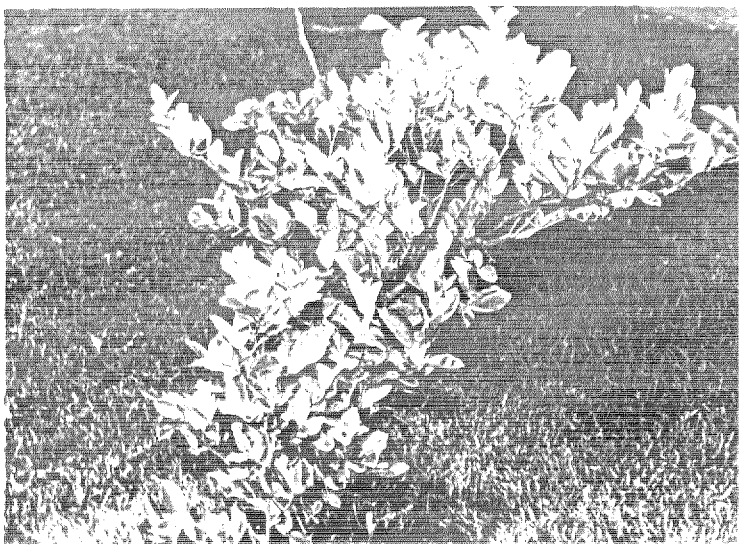
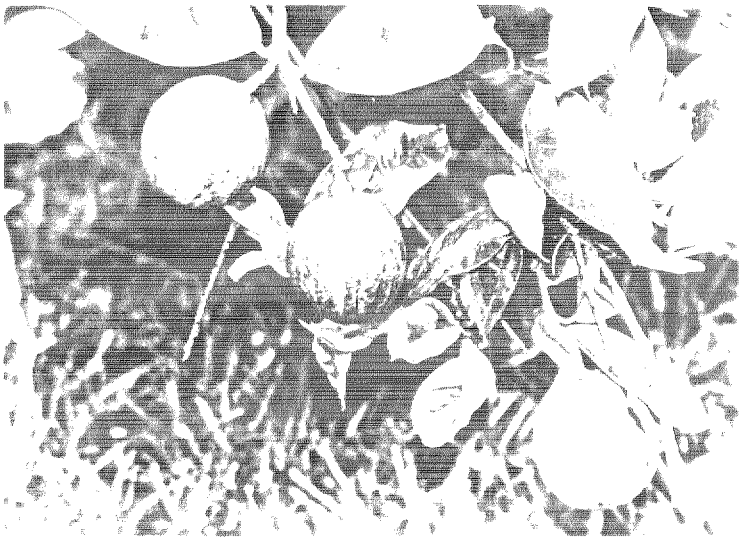
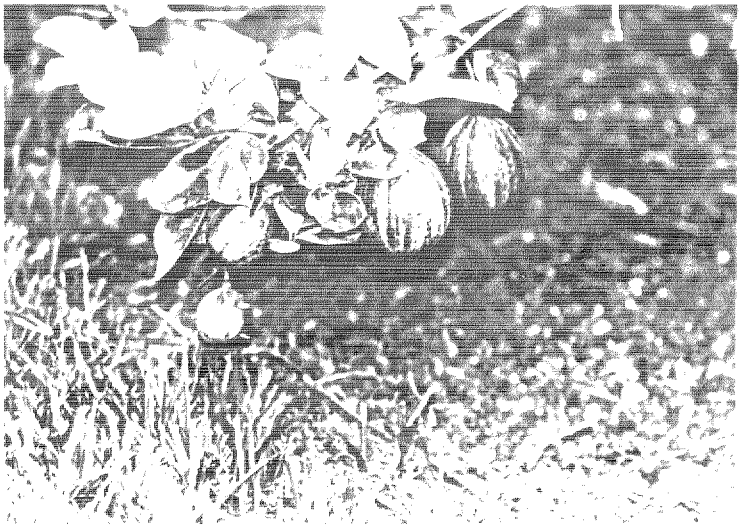

* * * * *